US012288607B2

United States Patent
Ko et al.

(10) Patent No.: US 12,288,607 B2
(45) Date of Patent: Apr. 29, 2025

(54) APPARATUS AND METHOD FOR UNSUPERVISED LEARNING-BASED MEDICAL DATA ANALYSIS

(71) Applicant: PROMEDIUS INC., Seoul (KR)

(72) Inventors: Jae Yeong Ko, Gunpo-si (KR); Hyun Jin Bae, Seoul (KR)

(73) Assignee: PROMEDIUS INC., Seoul (KR)

( * ) Notice: Subject to any disclaimer, the term of this patent is extended or adjusted under 35 U.S.C. 154(b) by 461 days.

(21) Appl. No.: 17/707,730

(22) Filed: Mar. 29, 2022

(65) Prior Publication Data

US 2023/0290484 A1    Sep. 14, 2023

Related U.S. Application Data

(63) Continuation of application No. PCT/KR2022/003690, filed on Mar. 16, 2022.

(30) Foreign Application Priority Data

Mar. 14, 2022    (KR) .................. 10-2022-0031193

(51) Int. Cl.
*G16H 30/20*    (2018.01)
*G06N 3/045*    (2023.01)
*G06V 10/774*    (2022.01)

(52) U.S. Cl.
CPC ............. *G16H 30/20* (2018.01); *G06N 3/045* (2023.01); *G06V 10/774* (2022.01)

(58) Field of Classification Search
CPC ....... G16H 30/20; G06V 10/774; G06N 3/045
See application file for complete search history.

(56) References Cited

U.S. PATENT DOCUMENTS

2020/0395124 A1* 12/2020 Karlin .................. G16H 30/40
2021/0106248 A1*  4/2021 Du ........................ G06T 11/60
2023/0109108 A1*  4/2023 Banerjee ............... G06N 3/088
                                                                  705/2

FOREIGN PATENT DOCUMENTS

KR    10-2018-0040287 A    4/2018

* cited by examiner

*Primary Examiner* — John J Lee
(74) *Attorney, Agent, or Firm* — Studebaker Brackett PLLC

(57) ABSTRACT

The present disclosure relates to an apparatus and a method for analyzing medical data based on unsupervised learning. By using a machine learning model based on an adversarial generative neural network to detect and notify anomalies in medical data, the present disclosure allows accurate and rapid reading, in addition to saving time and cost incurred by reading.

15 Claims, 9 Drawing Sheets

APPARATUS AND METHOD FOR UNSUPERVISED LEARNING-BASED MEDICAL DATA ANALYSIS

CROSS-REFERENCE TO RELATED APPLICATION

The present disclosure is a continuation of International Patent Application No. PCT/KR2022/003690, filed on Mar. 16, 2022, which is based upon and claims the benefit of priority to Korean Patent Application No. 10-2022-0031193 filed on Mar. 14, 2022. The disclosures of the above-listed applications are hereby incorporated by reference herein in their entirety.

BACKGROUND

1. Technical Field

The present disclosure relates to an apparatus and a method for unsupervised learning-based medical data analysis, and more specifically to, an apparatus and a method for unsupervised learning-based medical data to analyze medical data using a machine learning model trained based on unsupervised learning.

2. Description of Related Art

Artificial Intelligence (AI) is the field of computer science in which a computer imitates human intellectual behaviors. Even if the performance of the artificial intelligence is limited to imitating human intellectual behaviors, it is widely applied to the software-based field with the advantage of a high degree of accuracy, built by a wide range of data training, and rapid data processing speed that outperforms human behaviors.

Artificial intelligence is also applied to the medical field. Specifically, the technology for analyzing medical data based on artificial intelligence is positioned as a core technology that will lead the development of the medical data field.

In particular, a method in which AI algorithms are applied to medical images obtained from diagnostic apparatuses such as X-ray, ultrasound, Computed Tomography (CT), Magnetic Resonance Imaging (MRI), and Positron Emission Tomography (PET) machines to help clinicians make decisions is being developed.

In the case of auxiliary diagnostic systems determining whether tissue shown in medical data is normal or abnormal, and whether the patient is positive or negative for a tumor through artificial intelligence, it is known that the detection rate of lesions is improved, compared to the case in which only a radiologist reads the same medical data.

A machine learning algorithm may be used with an artificial intelligence algorithm, and the machine learning including supervised learning and unsupervised learning. Here, supervised learning may require correct answer labels regarding data to be trained for training the artificial intelligence-based machine learning model and what the data is. However, in unsupervised training, training may be performed only with data to be trained, without correct answer labels.

Supervised training is mainly used to predict specific diseases using medical data, and there may be a problem in which the supervised training accurately predicts training data distribution when training a model, but may not predict reliable information regarding newly distributed data. In addition, when training is performed using supervised training as described above, data to be trained and the correct answer label for the data are required. However, unlike other domains, due to the nature of a medical domain, when performing labeling on data, non-experts are not capable of performing a labeling work, so experts should perform the labeling work. Thus, a high volume of time and costs may be required.

Therefore, there is a need for developing technology to analyze medical data using an artificial intelligence-based machine learning model trained based on unsupervised learning.

RELATED ART

Patent Document (Patent Document 1) Korean Patent Application Publication No. 10-2018-0040287 (publication date: Apr. 20, 2018)

SUMMARY

There is provided an apparatus and a method for unsupervised learning-based medical data analysis to enable accurate and rapid reading and reducing time and costs generated by reading by detecting and notifying abnormalities in medical data using a machine-learning model based on an adversarial generative neural network.

The present disclosure is directed to providing an apparatus and a method for unsupervised learning-based medical data analysis to reduce false positives and perform anomaly detection with an artificial intelligence-based machine learning model using a multi-encoder including a first encoder for performing rapid anomaly detecting inference and a second encoder for extracting features described as normal.

The aspects to be solved by the present disclosure are not limited to the aspects mentioned above, and other aspects not mentioned will be clearly understood by those skilled in the art from the below.

According to an embodiment of the present disclosure, an unsupervised learning-based medical data analysis apparatus may include a communication module configured to collect first medical data for training based on wired-wireless communications, receive second medical data for reading a presence of a disease, and transmit and receive various types of data to and from an external apparatus, the first medical data and the second medical data each including at least one of: a generation module configured to, based on a multi-encoder, generate a pre-trained machine learning model by performing training on a machine learning model using the first medical data, and generate normal data, which is an image of a normal state based on the pre-trained machine learning module using the second medical data; a database configured to store the pre-trained machine learning model for analyzing medical data based on unsupervised learning, at least one medical data, and at least one process; and a control module configured to perform an operation for analyzing unsupervised learning-based medical data based on the at least one process, wherein the control module is configured to, in response to collecting the first medical data, perform training on the machine learning model by obtaining a feature value for the first medical data using the multi-encoder, and in response to receiving the second medical data, input a feature value to the pre-trained machine learning model by obtaining a feature value for the second medical data using the multi-encoder to control to determine whether the data is normal.

According to an embodiment of the present disclosure, a method for analyzing unsupervised learning-based medical data may include, in response to collecting first medical data, obtaining a feature value for the first medical data based on a multi-encoder and performing training on a machine learning model to generate a pre-trained machine learning model, and in response to receiving second medical data, obtaining a feature value for the second medical data using the multi-encoder and inputting the feature value to the pre-trained machine learning model to determine whether the data is normal, the first medical data and the second medical data each including at least one thereof, wherein the multi-encoder includes first and second encoders based on a convolutional neural network (CNN), the first encoder extracts regional and local features for the first and second medical data, and the second encoder exclusively modulizes features that are described as normal among from the extracted features and extracts only features that are described as completely normal.

The detailed description of the present disclosure will be described below with drawings.

According to the present disclosure, by detecting and notifying abnormalities in medical data using a machine learning model based on an adversarial generative neural network, accurate and rapid reading may be possible, as well as time and costs incurred by reading may be reduced.

In addition, according to the present disclosure, by training and using an artificial intelligence-based machine learning model using a first encoder for fast anomaly detection inference and a second encoder for extracting features that are described as normal, false positives may be lowered and anomaly detection may be performed.

Effects of the present disclosure are not limited to the above, and other effects not mentioned will be clearly understood by those skilled in the art from as below.

DETAILED DESCRIPTION

Figure 1:
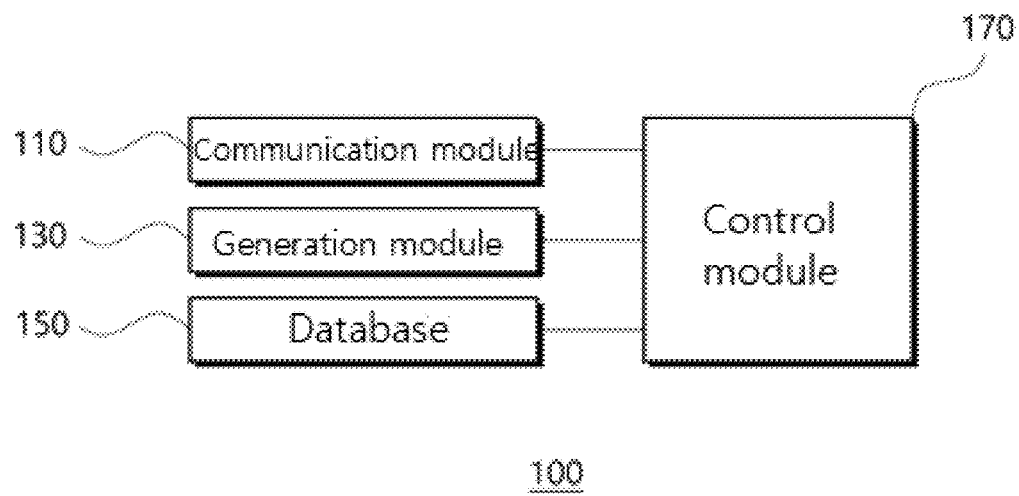
FIG. 1 is a block view illustrating configuration of an unsupervised learning-based medical data analysis apparatus according to an exemplary embodiment.

Advantages and features of the present disclosure and methods of achieving them may become apparent with reference to the embodiments described below in detail in association with the accompanying drawings. However, the present disclosure is not limited to the embodiments disclosed below, but may be implemented in various different forms, and only the embodiments thereof allow the disclosure of the present disclosure to be complete, and those of ordinary skill in the art to which the present disclosure pertains. It is provided to fully understand the scope of the present disclosure to those skilled in the art, and the present disclosure is only defined by the scope of the claims.

The present disclosure is not limited to embodiments disclosed below and may be implemented in various forms and the scope of the invention is not limited to the following embodiments. Furthermore, a singular form may include a plural from as long as it is not specifically mentioned in a sentence. Furthermore, "include/comprise" or "including/comprising" used in the specification represents one or more components, steps, operations, and elements exist or are added. Terms such as 'first' and 'second' may be used to describe various components, but they may not limit the various components. Those terms are only used for the purpose of differentiating a component from other components. For example, a first component may be referred to as a second component, and a second component may be referred to as a first component and so forth without departing from the spirit and scope of the present disclosure.

Unless otherwise defined, all terms including technical and scientific terms used herein have the same meaning as commonly understood by one of ordinary skill in the art to which the present disclosure belongs in view of the present disclosure. It will be further understood that terms, such as those defined in commonly used dictionaries, should be interpreted as having a meaning that is consistent with their meaning in the context of present disclosure and the relevant art, and will not be interpreted in an idealized or overly formal sense unless expressly so defined herein.

Spatially relative terms "below", "beneath", "lower", "above", "upper", etc. shall be used to easily describe the correlation between a component and other components. Spatially relative terms should be understood as terms including different directions of components during use or operation in addition to the directions shown in the drawings. For example, when a component shown in the drawings is turned over, a component described as "beneath" or "beneath" of another component may be placed "above" of the other component. Accordingly, the exemplary term "below" may include both directions below and above. Components may also be oriented in other directions, and thus spatially relative terms may be interpreted according to orientation.

As used herein, the term "unit" or "module" may refer to a hardware component such as software, FPGA, or ASIC, and "unit" or "module" may perform certain roles. However, "part" or "module" is not limited to software or hardware. A "unit" or "module" may be configured to reside on an addressable storage medium or to reproduce one or more processors. Thus, by way of example, "part" or "module" refers to components such as software components, object-oriented software components, class components and task components, processes, functions, properties, procedures, subroutines, segments of program code, drivers, firmware, microcode, circuitry, data, databases, data structures, tables, arrays and variables. Components and functionality provided within "parts" or "modules" may be combined into a smaller number of components and "parts" or "modules" or further separated as "parts" or "modules" with additional components.

Unless otherwise defined, all terms (including technical and scientific terms) used herein shall have the meaning commonly understood by those of ordinary skill in the art to which the present disclosure pertains. In addition, terms defined in a commonly used dictionary shall not to be interpreted ideally or excessively unless specifically defined explicitly.

The present disclosure aims to more accurately and rapidly read whether input medical data is normal or abnormal using a machine learning model trained based on unsupervised learning. Therefore, a machine learning model based on adversarial generative neural networks may be used, and a multi-encoder may be further used.

Hereinafter, referring to FIG. 1 to FIG. 10B, a detailed description of the present disclosure will be disclosed below.

FIG. 1 is a block view illustrating configuration of unsupervised learning-based medical data analysis apparatus according to an exemplary embodiment.

Referring to FIG. 1, an unsupervised learning-based medical data analysis apparatus 100 (referred to as "analysis apparatus") may include a communication module 110, a generation module 130, a database 150, and a control module 170.

The communication module 110 may perform communication with other apparatuses, and transmit and receive various types of data based wired communication based on wired communication, or various types of data based on wireless communication according to wireless Internet technology.

The wireless internet technology may include Wireless LAN (WLAN), Wireless-Fidelity (Wi-Fi), Wi-Fi Direct, Digital Living Network Alliance (DLNA), Wireless Broadband (WiBro), World Interoperability for Microwave Access (WiMAX), High Speed Downlink Packet Access (HSDPA), Long Term Evolution (LTE), Long Term Evolution-Advanced (LTE-A), etc. The analysis apparatus 100 may transmit and receive various types of data according to at least one wireless Internet technology within a range including internet technologies not listed above.

Short range communication may be supported using at least one of Bluetooth™, Radio Frequency Identification (RFID), Infrared Data Association (IrDA), Ultra Wideband (UWB), ZigBee, Near Field Communication (NFC), Wi-Fi, Wi-Fi Direct, and Wireless Universal Serial Bus (USB) technologies. Wireless communication between the analysis apparatus 100 and each different apparatus, equipment, and terminal may be supported through wireless area networks. In this case, the wireless area networks may be wireless personal area networks.

Specifically, the communication module 110 may collect first medical data for training, based on wired and wireless communication, or receive second medical data to read a presence of a disease. The first medical data and the second medical data each may include at least one thereof, or may be collected or received continuously, or periodically, or may not be limited thereto.

The generation module 130 may be based on a multi-encoder, and may generate a pre-trained machine learning model by performing training for a machine learning model using first medical data, or generate a normal data which is an image of a normal state based on the pre-trained machine learning model using second medical data.

A multi-encoder may include a plurality of encoders. For example, a vanilla encoder may be used as a first encoder, a memory encoder may be used as a second encoder. When only the vanilla encoder is used, there is an advantage that normal data of the input medical data may be well generated. However, due to the feature of generalization, when abnormal data is input, an image including up to a part including a defect may be generated. Therefore, in order to address this issue, a memory encoder may be further used. In other words, the vanilla encoder and the memory encoder may be simultaneously trained and used since in case of using only the vanilla encoder, false positive is relatively low, while generating normal data visually identical to the input medical data, but effective anomaly detection may not be performed due to a high possibility of anomalous features. Accordingly, it is possible to reduce false positives and perform anomaly detection more effectively than when using a single encoder.

Specifically, the vanilla encoder may extract regional and local features of the first medical data and/or the second medical data, and the memory encoder may exceptionally modulize features that are described as normal among the features extracted by the vanilla encoder, and extract only the features that are described completely normal.

A machine learning module may be based on generative adversarial networks including a generator and determinator.

The database 150 may store various types of data and/or information supporting various functions of the analysis apparatus 100. The database may store various application programs or application which operate in the analysis apparatus 100, data and commands for operating the analysis apparatus 100. At least part of the application programs may be downloaded from an external server through wireless communication. The application program may be stored in the control module 170, and mounted in the analysis apparatus 100 to perform operations (functions) by the control module 170.

Specifically, the database 150 may store a machine learning model for analyzing medical data based on unsupervised learning, a pre-trained machine learning model generated by training the machine learning model, and at least one process. The machine learning model and the pre-trained machine learning model generated by training the machine learning model may be at least one thereof, and may be selectively applied and used according to the case.

The database 150 may include a memory, and the memory may include a storage medium such as a flash memory type, a hard disk type, a multimedia card micro type, a card type memory (e.g. SD or XD memory), Random Access Memory (RAM), Static Random Access Memory (SRAM), Read-Only Memory (ROM), Electrically Erasable Programmable Read-Only Memory (EEPROM), Programmable Read-Only Memory (PROM), a magnetic memory, a magnetic disk, and an optical disk. In addition, the memory may store information temporarily, permanently, or semi-permanently, and may be provided as a built-in or removable type.

The control module 170 may process input or output signal, data, information, etc. by controlling all configurations in the analysis apparatus 100, or perform executing commands, algorithms, and application programs stored in the database 150 to perform various processes. In other words, the control module 150 may perform an operation for providing a security control service based on at least one process.

Specifically, the control 170 may be controlled to, in response to collecting the first medical data, obtain a feature value on the first medical data using a multi-encoder, and perform training on a machine learning model, and in response to receiving second medical data to read a presence of a disease, obtain a feature value for the second medical data using the multi-encoder to input the feature value to the pre-trained machine learning model, thereby determining whether the data is normal. The first medical data may be configured only with normal data, and the machine learning model may perform training using only the normal data.

The control module 170 may be controlled to, in response to perform training for a machine learning model, obtain a first feature value (Ze) by inputting the first medical data to the multi-encoder and performing information compression, and obtain a second feature value (Zê) by performing information compression by inputting again the third medical data generated by inputting the first feature value to a generator included in adversarial generative neural networks, thereby performing training while updating weights of the machine learning model by reducing a difference between the first feature value and the second feature value.

The control module 170 may be controlled to use a determinator included in the adversarial generative neural networks, perform determination on the first medical data and the third medical data, and update respective weights of the multi-encoder and the determinator.

The control module 170 may be controlled to obtain a feature value by performing information compression by inputting the second medical data to the multi-encoder, and input the feature value to the generator included in the adversarial generative neural networks, thereby determining whether the second medical data is normal. When the second medical data is determined to be abnormal, the control module 170 may detect an abnormal area from the second medical data, generate third medical data which is an image produced by restoring the abnormal area, and combine the third medical data with a residual image excluding the abnormal area from the second medical data, thereby generating and outputting normal data.

In addition, the control module 170 may extract an uncertainly rate for the abnormal area in a monte carlo dropout (MC dropout) method, generate an uncertainty map to match the uncertainty map to the normal data, and perform a correction for the uncertainty map, thereby removing the false positive. The uncertainty map may divide a difference between an image input to the first encoder and the generated image by pixel, and multiple a weight to the value to remove the false positive, thereby generating a normal image.

The control module 170 may determine whether the generated normal data is actual data or false data generated by the generator using a determinator included in the adversarial generative neural networks.

The control module 170 may calculate an abnormality score when determining whether the second medical data is normal, and calculate a specific threshold value for distinguishing a score above normal data and a score above abnormal data based on the abnormality score to determine whether the data is normal. When the second medical data is determined to be normal, the control module 170 may be controlled to exclude the second medical data.

Figure 2:
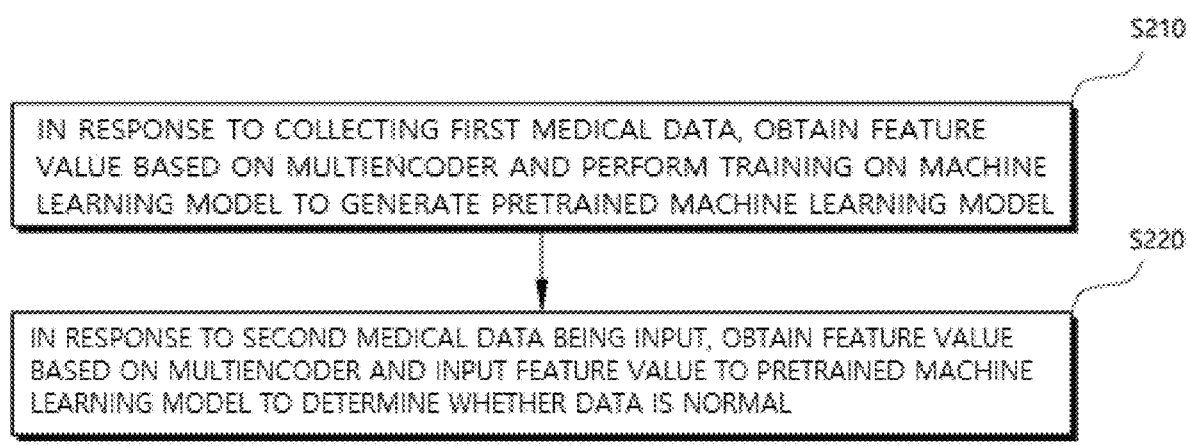
FIG. 2 is a flowchart illustrating a method for analyzing unsupervised learning-based medical data according to an exemplary embodiment.

FIG. 2 is a flowchart illustrating a method for analyzing unsupervised learning-based medical data according to an exemplary embodiment.

Referring to FIG. 2, the analysis apparatus 100 according to an embodiment of the present disclosure, in response to collecting the first medical data, may obtain a feature value for the first medical data using a multi-encoder to perform training for the machine learning model (S210).

In addition, the analysis apparatus 100, in response to receiving the second medical data, may obtain a feature value for the second medical data using a multi-encoder and input the feature value to the pre-trained machine learning model to determine whether the second medical data is normal (S220).

Figure 3:
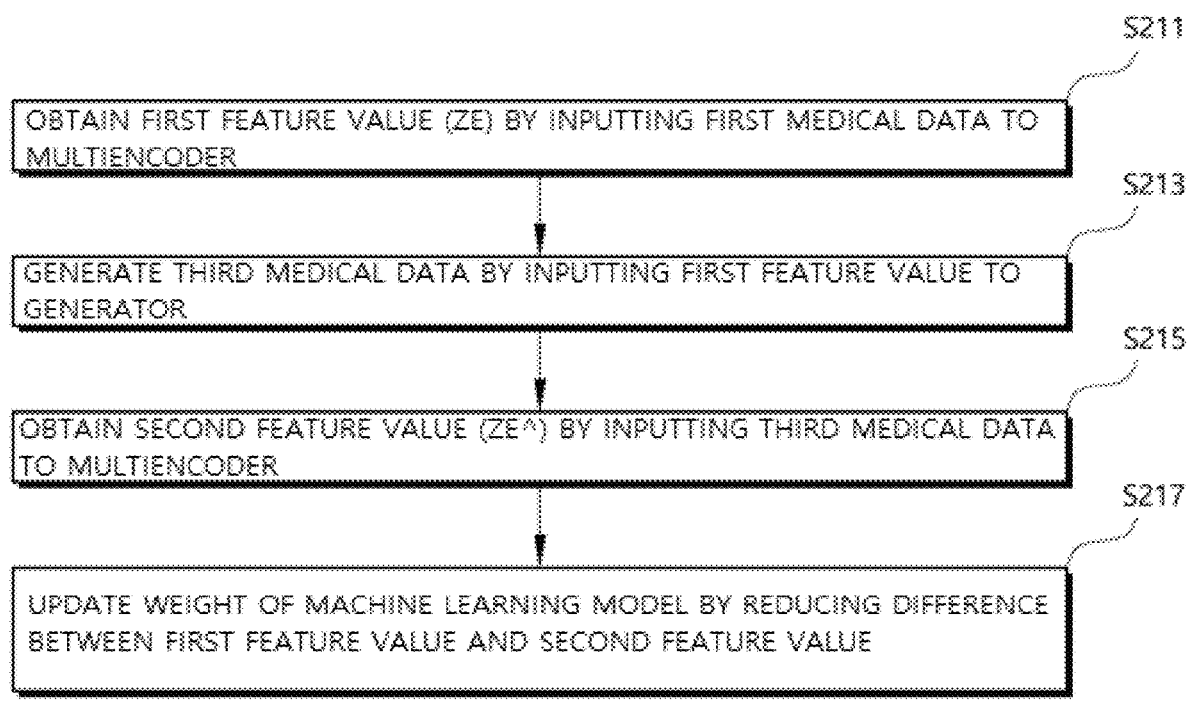
FIG. 3 is a flowchart illustrating a method for performing training for a machine learning model to analyze medical data according to an exemplary embodiment.

FIG. 3 is a flowchart illustrating a method for performing training for a machine learning model to analyze medical data according to an exemplary embodiment.

Referring to FIG. 3, the analysis apparatus 100 according to an embodiment of the present disclosure may obtain a first feature value (Ze) by performing information compression by inputting the first medical data collected to analyze the medical data to the multi-encoder (S211), and input the first feature value to the generator included in the adversarial generative neural networks to generate the third medical data (S213).

In addition, the analysis apparatus 100 may obtain a second feature value (Zê) by performing information compression by inputting again the third medical data generated in S213 in (S215), and update a weight of the machine leaning model to reduce a difference between the first feature value generated in S211 and the second feature value generated in S215 (S217). The function of the machine learning model may be further improved by repeatedly performing a series of operations as such.

Figure 4:
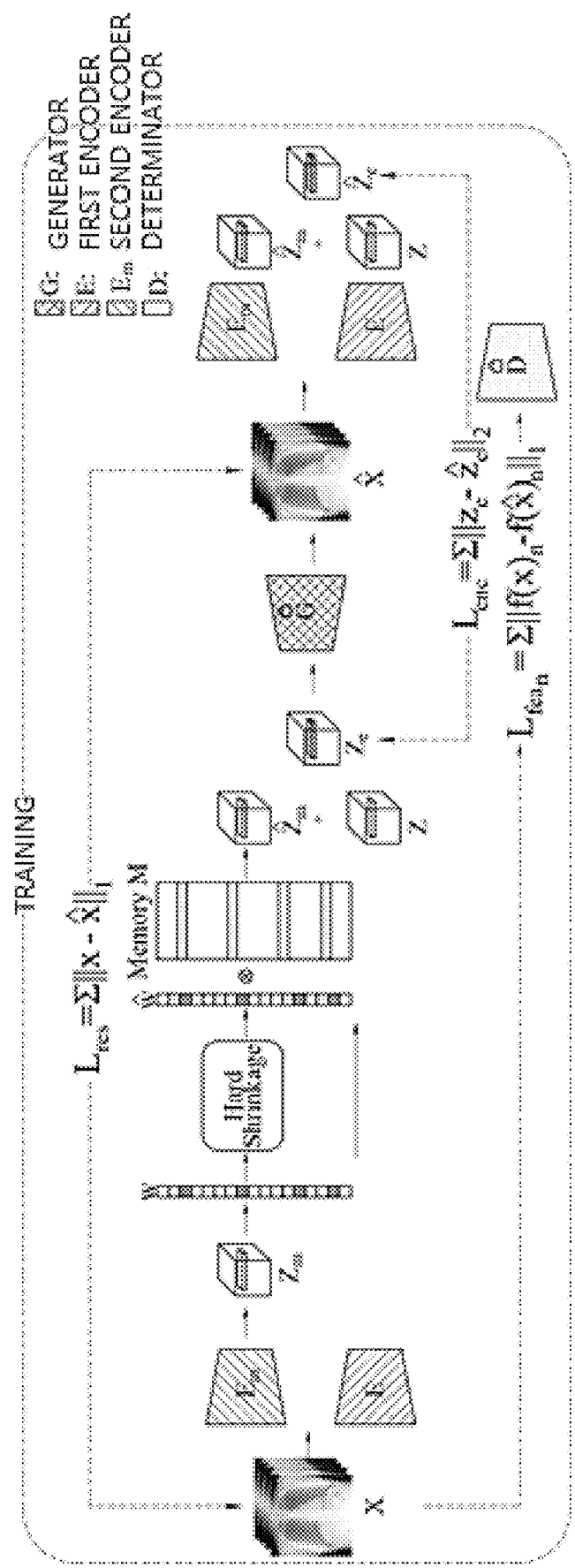
FIG. 4 is a view illustrating an example of procedure to process medical data when training for a machine learning model is performed according to an exemplary embodiment.

FIG. 4 is a view illustrating an example of a procedure to process medical data when performing training for a machine learning model according to an exemplary embodiment.

Referring to FIG. 4, the first medical data may penetrate a multi-encoder including a first encoder (E) and a second encoder (Em) to be information compressed with a latent vector, thereby obtaining the first feature value (Ze).

The obtained feature value may penetrate a generator (G) to generate false data, and again penetrate the multi-encoder including the first encoder (E) and the second encoder (Em) to be information compressed as a latent vector so that the second feature value (Zê) may be obtained. The false data may be medical data (the third medical data) generated by performing restoration on the features extracted from the first medical data.

Thereafter, the training may process while the weight of the machine learning model updates in a way that a difference between the first feature value (Ze) and the second feature value (Zê) is reduced.

The determinator (D) may update weights of the multi-encoder and the determinator (D) by determining actual data input for training and false data generated based on the first feature value (Ze).

Figure 5:
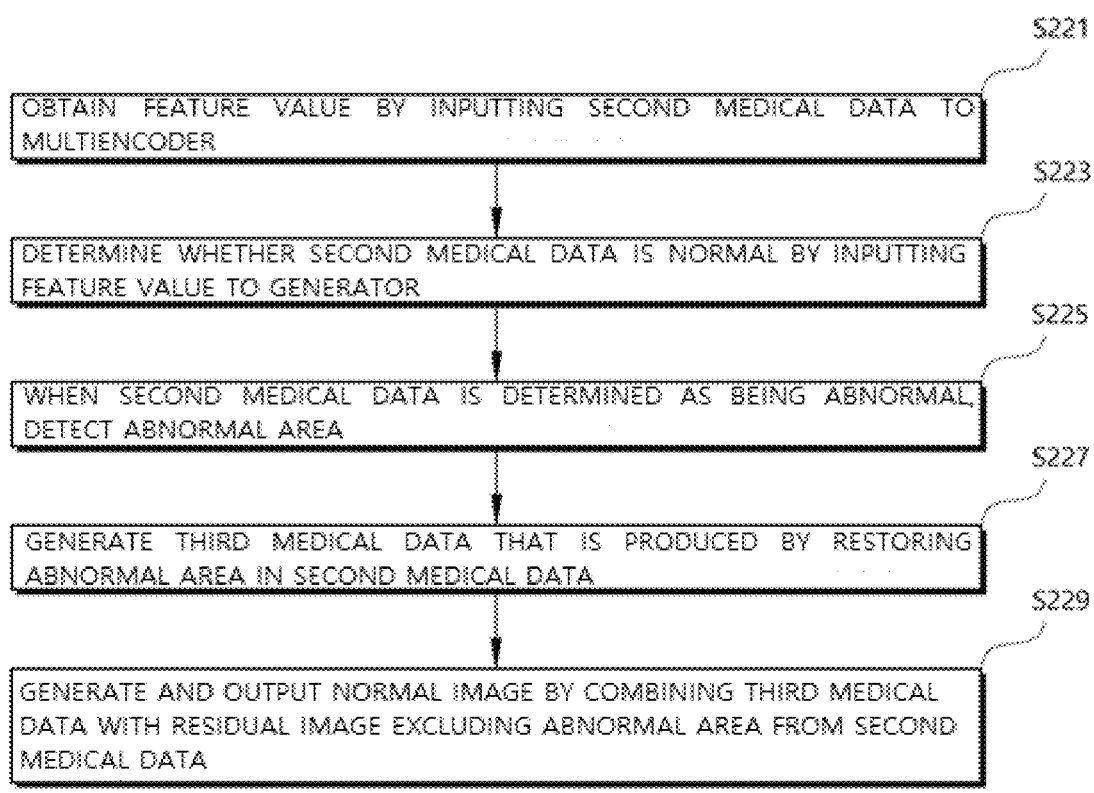
FIG. 5 is a flowchart illustrating a method for determining whether medical data is normal for diagnosing a presence of a disease based on pre-trained machine learning model to analyze medical data according to an exemplary embodiment.

FIG. 5 is a flowchart illustrating a method for determining whether medical data is normal for checking a presence of a disease based on pre-trained machine learning model to analyze medical data according to an exemplary embodiment.

Referring to FIG. 5, an analysis apparatus 100 may obtain a feature value by performing information compression by inputting the second medical data to read a presence of a disease to the multi-encoder (S221), and input the feature value to a generator included in adversarial generative neural networks to determine whether the second medical data is normal (S223).

As a result of determination, when the second medical data is determined to be abnormal, the analysis apparatus 100 may detect an abnormal area from the second medical data (S225), and generate the third medical data which is an image produced by restoring the abnormal area detected in S225 from the second medical data (S227).

In addition, the analysis apparatus 100 may combine the third medical data generated in S227 with a residual map excluding the abnormal area detected in S225 from the second medical data to generate and output normal data (S229).

Although not illustrated in FIG. 5, as a result of determination in S223, when the second medical data is determined to be a normal image, the data may be excluded.

Figure 6:
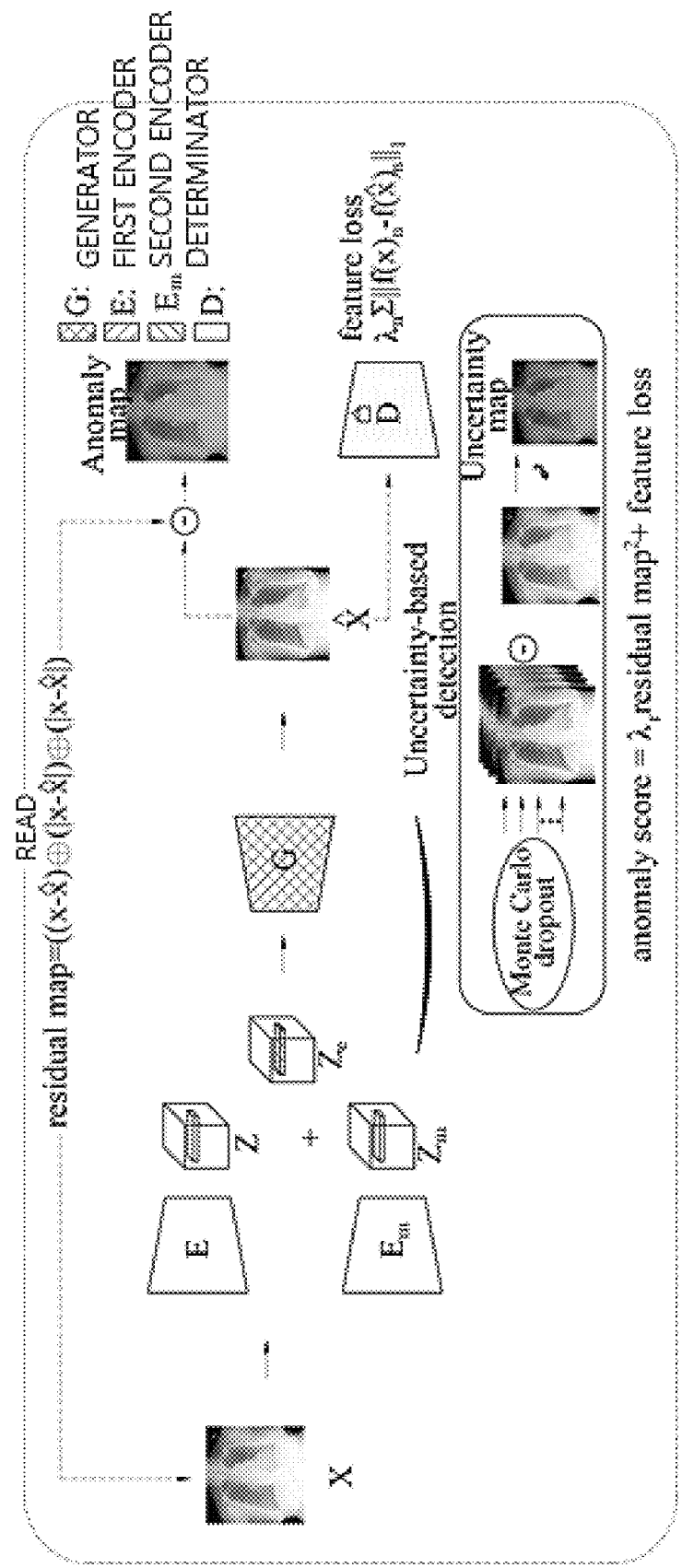
FIG. 6 is a view illustrating an example of a procedure to process medical data for determining whether the data is normal based on the pre-trained machine learning model according to an exemplary embodiment.
Figure 7A:
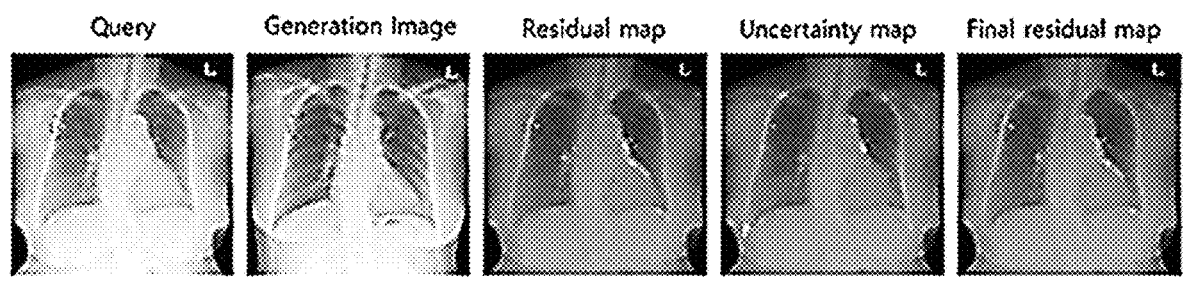
FIGS. 7A to 10B are views illustrating an example of analyzed medical data of two patients suffering from diseases, respectively using an unsupervised learning-based medical data analysis apparatus according to an exemplary embodiment.
Figure 7B:
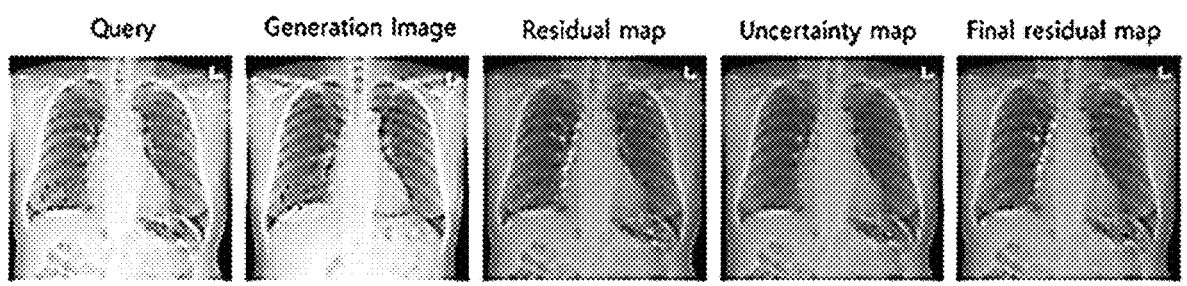
Figure 8A:
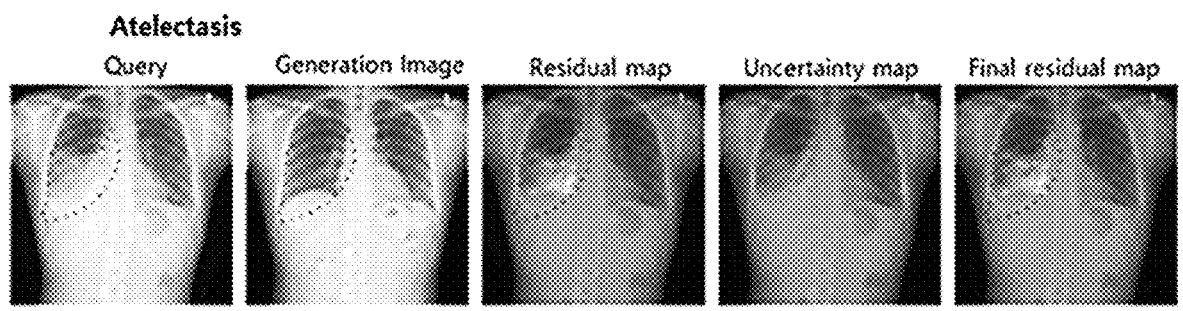
Figure 8B:
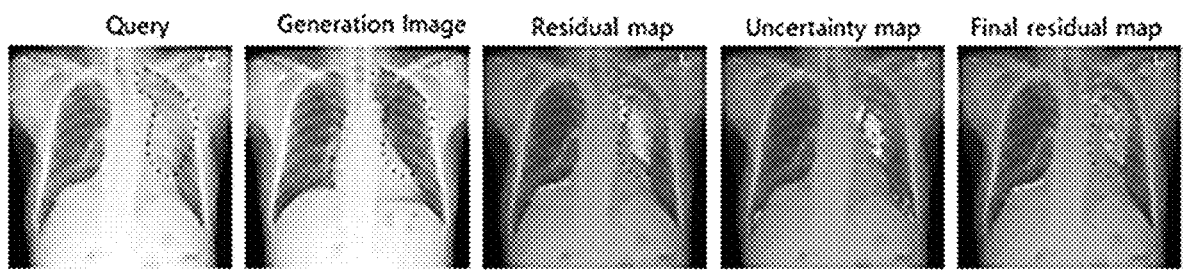
Figure 9A:
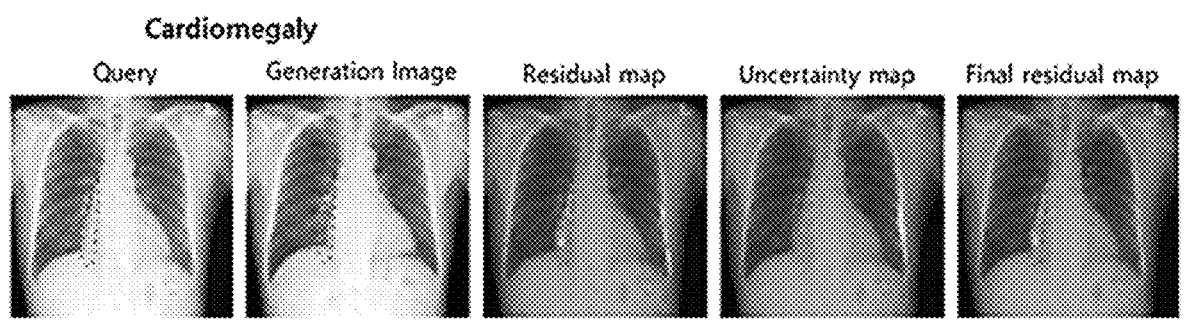
Figure 9B:
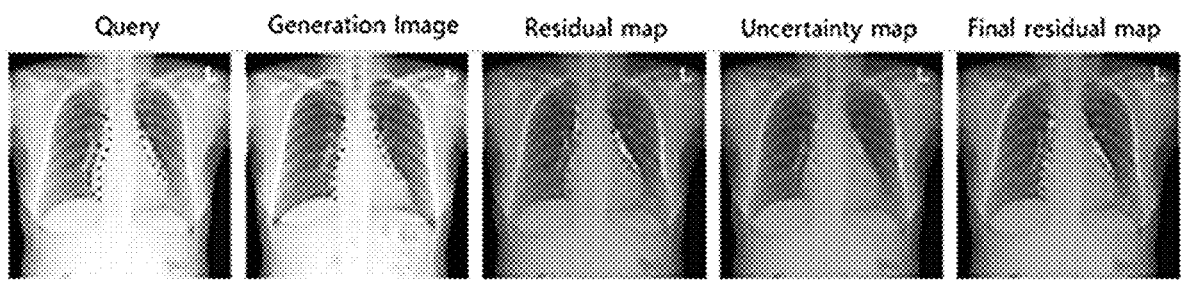
Figure 10A:
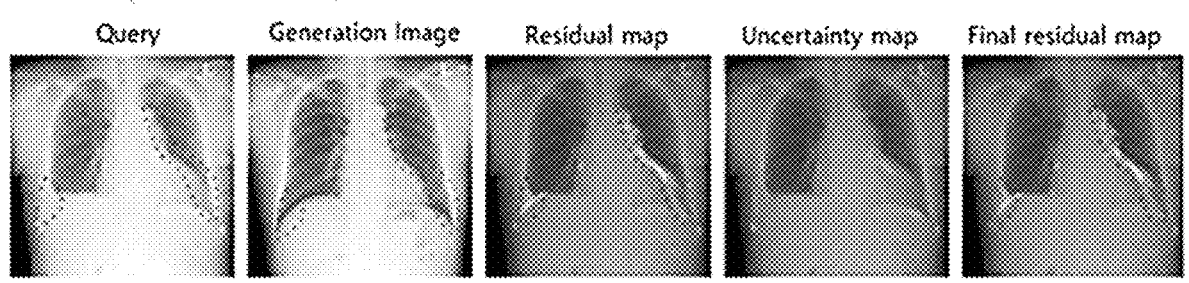
Figure 10B:
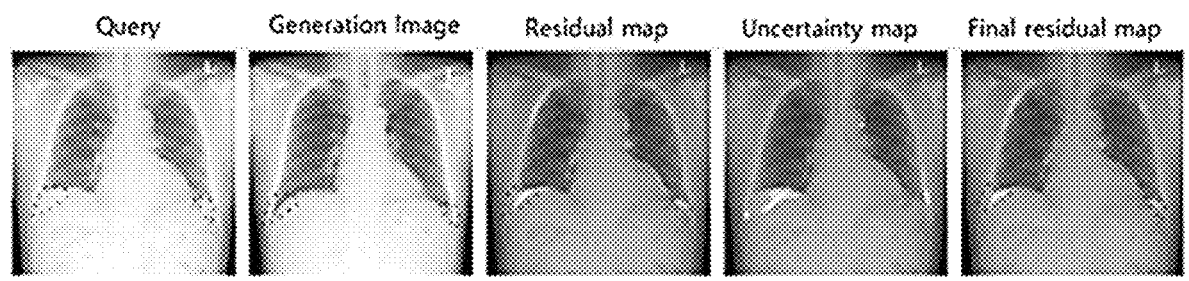

FIG. 6 is a view illustrating an example of a procedure to process medical data for determining whether the data is normal based on the pre-trained machine learning model according to an exemplary embodiment.

Referring to FIG. 6, the second medical data for reading a presence of a disease may penetrate the multi-encoder including a first encoder (E) and a second encoder (Em), and obtain a specific value (Ze) as information compression is performed as a latent vector.

The obtained feature value may penetrate a generator (G) to generate false data, and penetrate the multi-encoder including the first encoder (E) and the second encoder (Em), and obtain a second feature value (Ze^) since the information compression is performed as the latent vector.

The obtained feature value may penetrate the generator (G) to generate false data, and combine the false data with a residual image excluded by detecting an abnormal area from the second medical data, thereby generating normal data. The false data is medical data (the third medical data) generated by performing restoration on a feature extracted from the second medical data.

In addition, based on the abnormality score, the second medical data may be divided into normal data or abnormal data. The abnormality score may be calculated regarding how different the abnormal data is compared to the normal data. Therefore, a specific threshold value that distinguishes between a score above normal data and a score above abnormal data may be calculated, and then medical data may be excluded first.

FIGS. 7A to 10B are views illustrating an example of analyzed medical data of two patients suffering from diseases, respectively using an unsupervised learning-based medical data analysis apparatus according to an exemplary embodiment. Medical data of two patients A and B with calcification, atelectasis, cardiomegaly and pleural effusion, respectively, are shown.

Information on medical data input as a query may be input into a pre-trained machine learning model to read whether the medical data is normal. The presence of a lesion may be identified through whether the predicted medical data is normal.

In detail, a generalized image may be generated through generalization of medical data input as a query, and a residual map may be generated excluding an abnormal area detected from the generalized image. Thereafter, a final normal image map may be generated by generating an uncertainty map for the previously detected abnormal area, combing the uncertainty map with the generalized image, and removing false positives by performing correction on the uncertainty map.

The method according to an embodiment of the present disclosure described above may be implemented as a program (or application) to be executed in combination with a server, which is hardware, and stored in a medium.

The above-described program may include code that is coded in the computer language such as C, C++, JAVA, machine language, etc. that a processor (CPU) of the computer reads through a device interface of the computer in order for the computer to read the program and execute the methods implemented as a program. The code may include functional code related to a function defining functions necessary for executing the methods, etc., and include an execution procedure related control code necessary for the processor of the computer to execute the functions according to a predetermined procedure. In addition, the code may further include a memory reference related code regarding where additional information or media necessary for the processor of the computer to execute the functions is located in the internal or external memory of the computer. In addition, when the processor of the computer needs to communicate with any other computer or server in a remote location in order to execute the functions, the code may further include a communication related code regarding to determine how to communicate with any other computer or server remotely using the communication module of the computer or which information or media is transmitted or received while communication.

The storage medium may not be a medium that stores data for a short moment, such as a register, a cache, a memory, etc., but a medium that stores data semi-permanently and is read by a device. Specifically, examples of the storage medium may include ROM, RAM, CD-ROM, magnetic tape, floppy disk, and optical data storage device, but is not limited thereto. The program may be stored in various recording media on various servers that the computer accesses or in various recording media on the user's computer. In addition, the medium may be distributed in a computer system connected to a network, and a computer-readable code may be stored in a distributed manner.

The steps of a method or an algorithm described in connection with an embodiment of the present disclosure may be implemented directly as hardware, as a software module executed by hardware, or as a combination thereof. A software module may include random access memory (RAM), read only memory (ROM), erasable programmable ROM (EPROM), electrically erasable programmable ROM (EEPROM), flash memory, hard disk, removable disk, CD-ROM, or any type of computer-readable recording medium well known in the art to which the present disclosure pertains.

In the above, embodiments of the present disclosure are described with reference to the accompanying drawings, but those of ordinary skill in the art to which the present disclosure pertains may understand that the present disclosure may be embodied in other specific forms without changing the technical spirit or essential features thereof. Therefore, it shall be understood that the embodiments described above are illustrative in all respects and not limited thereto.

DESCRIPTION OF REFERENCE

100: ANALYSIS APPARATUS
110: COMMUNICATION MODULE
130: GENERATION MODULE
150: DATABASE
170: CONTROL MODULE

The invention claimed is:
1. An unsupervised learning-based medical data analysis apparatus, comprising:
a communication module configured to collect first medical data for training based on wired-wireless communications, receive second medical data for reading a presence of a disease, and transmit and receive various types of data to and from an external apparatus;

a generation module configured to, based on a multi-encoder, generate a pre-trained machine learning model by performing training on a machine learning model using the first medical data, and generate normal data which is an image of a normal state based on the pre-trained machine learning module using the second medical data;

a database configured to store the pre-trained machine learning model for analyzing medical data based on unsupervised learning, and at least one medical data; and a control module configured to perform an operation for analyzing unsupervised learning-based medical data, wherein the control module is configured to, in response to collecting the first medical data, perform training on the machine learning model by obtaining a feature value for the first medical data using the multi-encoder, and in response to receiving the second medical data, input a feature value to the pre-trained machine learning model by obtaining a feature value for the second medical data using the multi-encoder to control to determine whether the data is normal.

2. The apparatus as claimed in claim 1, wherein the multi-encoder includes first and second encoders based on a convolutional neural network (CNN), wherein the first encoder extracts regional or local features for the first and second medical data, and wherein the second encoder exclusively modulizes features that are described as normal among from the extracted features, and extracts only features that are described as completely normal.

3. The apparatus as claimed in claim 2, wherein the machine learning model is based on generative adversarial networks including a generator and a determinator, and wherein the control module is configured to control to, in response to performing training on the machine learning model, obtain a first feature value (Ze) by performing information compression by inputting the first medical data to the multi-encoder, obtain a second feature value (Ze^) by performing information compression by inputting again third medical data generated by inputting the first feature value to the generator to the multi-encoder, and perform the training while updating a weight of the machine learning model by reducing a difference between the first feature value and the second feature value.

4. The apparatus as claimed in claim 3, wherein the control model is configured to control to update a weight of each of the multi-encoder and the determinator by determining the first medical data and the third medical data.

5. The apparatus as claimed in claim 2, wherein the pre-trained machine learning model is based on generative adversarial networks including a generator and a determinator, and wherein the control module is configured to control to, obtain the feature value by performing information compression by inputting the second medical data to the multi-encoder, determine whether the second medical data is normal by inputting the feature value to the generator, when the second medical data is determined to be abnormal, detect an abnormal area from the second medical data, generate third medical data which is an image produced by restoring the abnormal area, and generate and output the normal data by combining the third medical data with a residual image produced by excluding the abnormal area from the second medical data.

6. The apparatus as claimed in claim 5, wherein the control module is configured to calculate an uncertainty rate for the abnormal area in a monte carlo dropout (MC dropout) method, generate an uncertainty map to combine the uncertainty map with the normal data, and remove a false positive by performing correction on the uncertainty map, and wherein the determinator is configured to determine whether the normal data is actual data or false data generated by the generator.

7. The apparatus as claimed in claim 1, wherein the control module is configured to, when determining whether the second medical data is normal, calculate an abnormality score, and calculate a specific threshold value for determining a score above normal data or a score above abnormal data based on the abnormality score to determine whether the data is normal, and when the second medical data is determined to be normal, exclude the second medical data.

8. A method for analyzing unsupervised learning-based medical data, the method being performed by an apparatus and comprising:

in response to receiving reading medical data for reading a presence of a disease, obtaining a feature value for the reading medical data using a multi-encoder, and inputting the feature value to a pre-trained machine learning model to determine whether the data is normal or abnormal;

when the reading medical data is determined to be abnormal, detecting an abnormal area from the reading medical data;

generating restored medical data by restoring the abnormal area; and excluding the abnormal area from the reading medical data, and generating normal data by combining the restored medical data with the reading medical data in which the abnormal area is excluded.

9. The method as claimed in claim 8, wherein the multi-encoder includes a first encoder and a second encoder based on convolutional neural network (CNN), wherein the first encoder is configured to extract a regional or local feature for first medical data for training of the pre-trained machine learning model, and extract the second medical data that is the reading medical data for reading the presence of the disease, and wherein the second encoder is configured to exclusively modulize features that are described as normal among the extracted features, and extract only features that are described as completely normal.

10. The method as claimed in claim 9, wherein the machine learning model is based on generative adversarial networks including a generator and a determinator, and wherein the method comprises, in response to performing training on a machine learning model, obtaining a first feature value (Ze) by performing information compression by inputting the first medical data to the multi-encoder, obtaining a second feature value (Ze^) by performing information compression by inputting again third medical data that is the restored medical data and is generated by inputting the Ze to the generator to the multi-encoder, and performing the training while updating a weight of the machine learning model by reducing a difference between the first feature value and the second feature value.

11. The method as claimed in claim 10, wherein when the weight of the machine learning model is updated, a weight of each of the multi-encoder and the determinator is also controlled to be updated by discriminating the first medical data and the third medical data.

12. The method as claimed in claim 9, wherein the pre-trained machine learning model is based on generative adversarial networks including a generator and a determinator, and wherein the method comprises, in response to determining whether data is normal based on the pre-trained machine learning model, obtaining the feature value by performing information compression by inputting the second medical data to the multi-encoder, determining whether the second medical data is normal by inputting the feature value to the generator, when the second medical data is determined to be abnormal, detecting the abnormal area from the second medical data, generating third medical data which is the restored medical data and is an image produced by restoring the abnormal area, and generating and outputting the normal data by combining the third medical data with a residual map excluding the abnormal area from the second medical data.

13. The method as claimed in claim 12, wherein the method comprises, in response to generating and outputting the normal data, calculating an uncertainty map for the abnormal area in a monte carlo dropout (MC dropout) method and generating an uncertainty map to combine the uncertainty map with the normal data, and removing a false positive by performing correction on an uncertainly map, wherein the determinator determines whether the normal data is actual data or false data generated by the generator.

14. The method as claimed in claim 8, wherein the method comprises, in response to determining whether the reading medical data is normal, calculating an abnormality score, calculating a specific threshold value for distinguishing a score above normal data and a score above abnormal data based on the abnormality score to determine whether the data is normal, and when the reading medical data is determined to be normal, excluding the reading medical data.

15. A computer readable recording medium wherein an unsupervised learning-based medical data analysis program to enable a computer to perform a method of claim 8 is recorded.

* * * * *